(12) United States Patent
Gondal et al.

(10) Patent No.: US 9,034,169 B2
(45) Date of Patent: *May 19, 2015

(54) METHOD FOR DETECTION OF CYANIDE IN WATER

(71) Applicant: KING FAHD UNIVERSITY OF PETROLEUM AND MINERALS, Dhahran (SA)

(72) Inventors: Mohammed Ashraf Gondal, Islamabad (PK); Qasem Ahmed Qasem Drmosh, Ibb (YE); Z. H. Yamani, Dhahran (SA); Tawfik Abdo Saleh, Hidadah (YE)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 13/827,999

(22) Filed: Mar. 14, 2013

(65) Prior Publication Data

US 2013/0203178 A1      Aug. 8, 2013

Related U.S. Application Data

(63) Continuation of application No. 12/801,547, filed on Jun. 14, 2010, now Pat. No. 8,460,538.

(51) Int. Cl.
*G01N 27/26* (2006.01)
*G01N 27/30* (2006.01)
*G01N 27/416* (2006.01)
*G01N 33/18* (2006.01)
*C01B 15/047* (2006.01)

(52) U.S. Cl.
CPC ....... *G01N 27/30* (2013.01); *Y10T 436/172307* (2015.01); *G01N 27/4166* (2013.01); *G01N 33/182* (2013.01); *C01B 15/047* (2013.01); *Y10S 977/773* (2013.01)

(58) Field of Classification Search
CPC .............................. G01N 27/30; C01B 15/047
USPC ................ 205/780.5, 775; 977/773, 889, 957
See application file for complete search history.

(56) References Cited

U.S. PATENT DOCUMENTS

| 3,272,728 A | 9/1966 | Rahndorfr et al. |
| 4,732,609 A | 3/1988 | Frey et al. |
| 4,737,289 A | 4/1988 | Castaldi et al. |

(Continued)

OTHER PUBLICATIONS

"Cyanide Treatment," U.S. Peroxide web site, www.h202.com/industrial/applications.aspx?pid-name-Cyanide-Treatment, printed May 20, 2010.

*Primary Examiner* — Luan Van
*Assistant Examiner* — Gurpreet Kaur
(74) *Attorney, Agent, or Firm* — Richard C Litman

(57) ABSTRACT

The method for detection of cyanide in water is a method for the detection of a highly toxic pollutant, cyanide, in water using $ZnO_2$ nanoparticles synthesized locally by an elegant Pulsed Laser Ablation technique. $ZnO_2$ nanoparticles having a median size of 4 nm are synthesized from pure zinc metal target under UV laser irradiation in a 1-10% $H_2O_2$ environment in deionized water. The synthesized $ZnO_2$ nanoparticles are suspended in dimethyl formamide in the presence of Nafion, and then ultrasonicated to create a homogenous suspension, which is used to prepare a thin film of $ZnO_2$ nanoparticles on a metal electrode. The electrode is used for cyanide detection.

1 Claim, 7 Drawing Sheets

(56) References Cited

U.S. PATENT DOCUMENTS

| | | |
|---|---|---|
| 5,264,192 A | 11/1993 | Shutt et al. |
| 7,413,725 B2 | 8/2008 | El-Shall et al. |
| 7,423,512 B1 | 9/2008 | Reitz et al. |
| 8,460,538 B2 * | 6/2013 | Gondal et al. ............ 205/780.5 |
| 2006/0145306 A1 * | 7/2006 | Lee et al. ............ 257/643 |
| 2007/0065595 A1 * | 3/2007 | Yamada et al. ............ 427/534 |
| 2007/0095407 A1 * | 5/2007 | Chen et al. ............ 137/597 |
| 2008/0280372 A1 | 11/2008 | Walker et al. |
| 2009/0258429 A1 | 10/2009 | Raymo et al. |

* cited by examiner

METHOD FOR DETECTION OF CYANIDE IN WATER

CROSS-REFERENCE TO RELATED APPLICATIONS

This application is a continuation of my prior application Ser. No. 12/801,547, filed Jun. 14, 2010, now U.S. Pat. No. 8,460,538.

BACKGROUND OF THE INVENTION

1. Field of the Invention

The present invention relates to water quality testing methods, and particularly to a method for detection of cyanide in water, to an electrode used in the method that has a coating of a thin film of $ZnO_2$ nanoparticles thereon, and to a method of forming $ZnO_2$ nanoparticles by laser ablation.

2. Description of the Related Art

Cyanide is used in many industrial applications, such as electroplating, precious metal refining, metal mining, metal ore processing, smelting, and other chemical and petrochemical applications.

Exposure to cyanide ions can occur through inhalation, ingestion, eye or skin contact, and absorption through the skin, eyes, and mucous membranes. It can cause rapid death due to metabolic asphyxiation. Cyanide is extremely toxic, and even relatively small amounts of this species are lethal to humans. The toxicity of cyanide results from its propensity to bind the iron in cytochrome c oxidase, interfering with electron transport and resulting in hypoxia. Death can occur within seconds or minutes of the inhalation of high concentrations of hydrogen cyanide gas. A recent study reports that 270 ppm is fatal after 6 to 8 minutes, 181 ppm after 10 minutes and 135 ppm after 30 minutes. Cyanide directly stimulates the chemoreceptor of the carotid and aortic bodies, causing hyperpnea. Cardiac irregularities are often noted. Industrial exposure to hydrogen cyanide solutions has caused dermatitis, itching, scarlet rash, papules, and nose irritation and bleeding. Perforation of the nasal septum has also occurred.

Thus, there exists a need for an efficient sensing system for cyanide to monitor cyanide concentration from contaminant sources.

The Environmental Protection Agency (EPA) has set the maximum contaminant level (MCL) for cyanide as free cyanide (which includes both hydrogen cyanide [HCN] and $CN^-$ ions) at 0.2 mg/L to regulate the safe levels for drinking water. Different methods have been reported in literature for free cyanide detection, including amenable cyanide (Standard Methods SM-4500-G) [8] with either titration SM-4500-D), colorimetric SM-4500-E), or ion selective electrode (ISE) (SM4500-CN-F) detection methods, and free cyanide detected directly by an ISE. Other methods in current use for determination of cyanide include titration, colorimetric, ion selective electrode, ion chromatography methods and Raman and IR spectroscopy. However, each of these methods has one or more problems associated therewith.

Using laser to ablate materials has been applied in laser-based materials processing for many years. Recently, two popular methods have been developed in nanomaterials preparations: pulsed laser ablation deposition (PLAD) to prepare thin films, and pulsed laser ablation (PLA) to produce nanoparticles, nanorods and nanotubes in liquids. PLA of solid target in a liquid medium has been used for preparing metal, metal oxide, and alloy nanoparticles. However, most of these processes rely on ablation onto solid target that produce not very high yield.

Metal oxide nanoparticles provide a favorable conducive environment for molecules to transfer electrons with underlying electrodes because of the structure stability and small size of inorganic nanoparticles, which provide a larger surface area than plating. Moreover, the small pores in metal oxide could act as a substrate containing transport channels to decrease mass transfer resistance for efficient mobility of charged species, which could enhance the sensitivity of an electrode.

Thus, a method for detection of cyanide in water solving the aforementioned problems is desired.

SUMMARY OF THE INVENTION

The method for detection of cyanide in water is a method for the detection of a highly toxic pollutant, cyanide, in water using $ZnO_2$ nanoparticles synthesized locally by an elegant Pulsed Laser Ablation technique. $ZnO_2$ nanoparticles having a median size of 4 nm are synthesized from pure zinc metal target under UV laser irradiation in a 1-10% $H_2O_2$ environment in deionized water. The synthesized $ZnO_2$ nanoparticles are suspended in dimethyl formamide in the presence of Nafion, and then ultrasonicated to create a homogenous suspension, which is used to prepare a thin film of $ZnO_2$ nanoparticles on a metal electrode. The electrode is used for cyanide detection.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method for detection of cyanide in water is a method for the detection of a highly toxic pollutant, cyanide, in water using $ZnO_2$ nanoparticles synthesized locally by an elegant Pulsed Laser Ablation technique. $ZnO_2$ nanoparticles having a median size of 4 nm are synthesized from pure zinc metal target under UV laser irradiation in a 1-10% $H_2O_2$ environment in deionized water. The synthesized $ZnO_2$ nanoparticles are suspended in dimethyl formamide in the presence of Nafion, and then ultrasonicated to create a homogenous suspension, which is used to prepare a thin film of $ZnO_2$ nanoparticles on a metal electrode. The electrode is used for cyanide detection. The foregoing principles are illustrated by the following example.

Example

Figure 1:
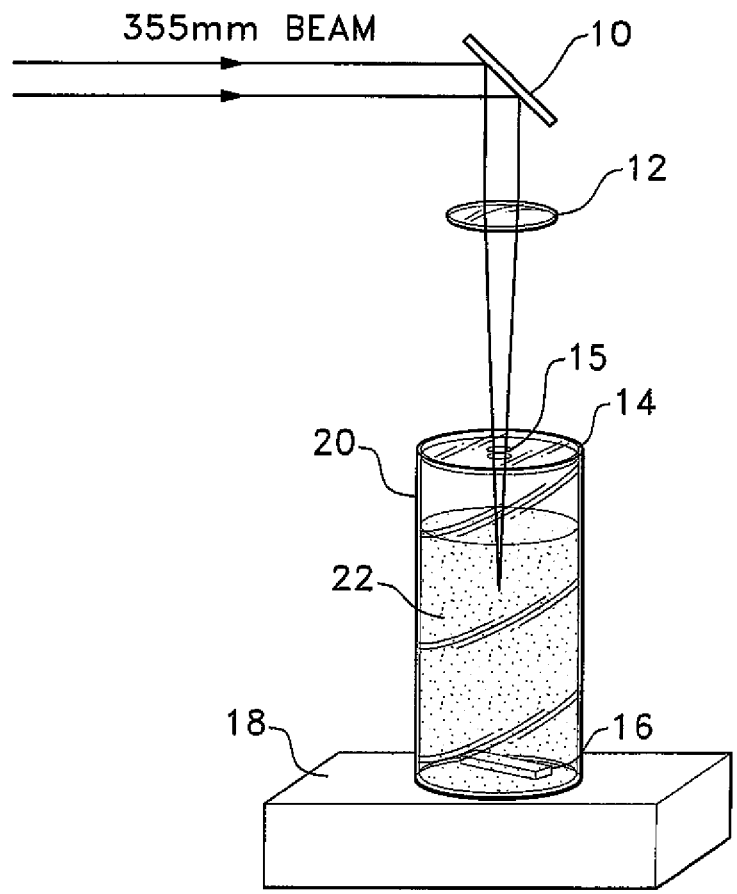
FIG. 1 is a schematic diagram of an experimental set up for synthesis of $ZnO_2$ nanoparticles by laser ablation.

For the synthesis of nanosize ZnO particles, a laser-based setup was designed and constructed, as shown in FIG. 1. For ablation of zinc particles in pure de-ionized water, a Q-switched Nd-YAG laser operating at 355 nm wavelength using a third harmonic generator was employed. This laser can deliver pulse energy of 1-300 mJ with a pulse width of 8 ns and operates at a 10 Hz pulse repetition rate. The collimated beam is tightly focused on the target sample of zinc metal using a mirror 10 and convex lens 12 to create a spark or breakdown in the sample. The laser energy was measured with a calibrated energy meter (Ophir model 300) for the study of dependence of nanoparticle yield on incident laser energy. In order to get a uniform laser beam shape, a 2 mm diameter aperture 15 was formed in the glass cell cover 14, which was placed in the path of the laser beam.

For the synthesis of nanoparticles, a high-purity metallic zinc foil, 1 mm thick and having a purity of 99.99% (Sigma Aldrich Company) was fixed on a magnetic holder 16 at the bottom of a glass cell 20 as the target, and was rotated using a magnetic stirrer 18 to avoid deep ablation crusts. In addition to the use of zinc foil, high purity (99.999%) metallic zinc powder was also applied for the synthesis of $ZnO_2$ nanoparticles. For this purpose, microstructured zinc particles were suspended in 3% $H_2O_2$, which resulted in better yield and higher quality of $ZnO_2$. The laser beam was focused by a lens 12 with a focal length of 250 mm in order to get sufficient laser intensity for ablation. The typical diameter of the laser spot on a bulk target was ~0.08 mm, and the typical liquid volume in the container 20 was 10 ml of 3% $H_2O_2$ in deionized water. The addition of an oxidizing agent like $H_2O_2$ helps in synthesis and conversion of ZnO to $ZnO_2$.

After 40 minutes laser irradiation time, a milky colloidal solution 22 of peroxide-based nanoparticles was obtained. The colloidal suspension was separated from the water after laser irradiation using a centrifuge.

The structure and grain size of the zinc peroxides produced by laser ablation were characterized by using X Ray Diffraction (Shimadzu XRD Model 6000). A typical size of the zinc peroxide nanoparticles of about 4 nanometers was achieved with this method.

The UV-VIS optical absorbance spectra of the zinc oxide nanoparticles were recorded at room temperature using a JASCO V-570 spectrophotometer for bandgap determination of $ZnO_2$. The photoluminescence spectra were studied using a spectrofluorometer (Shimadzu RF-5301 PC) equipped with 150 W Xenon lamp as the excitation source. The nanopowders were also characterized by infrared spectroscopy (FTIR-100 Spectrometer using KBr pellets).

Figure 2:
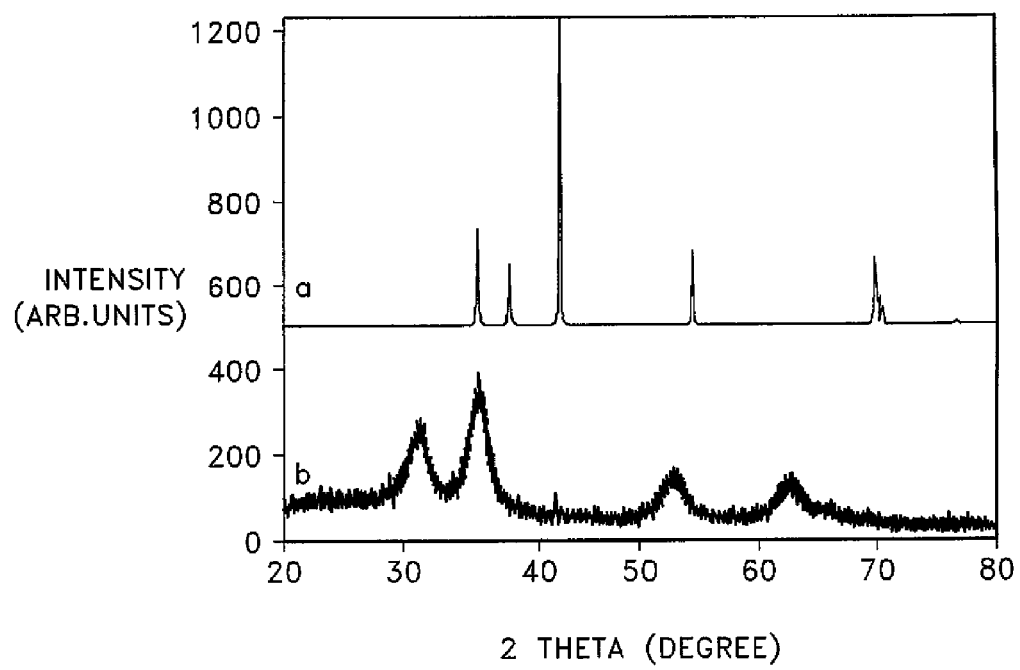
FIG. 2 shows the X-ray diffraction spectrum of micro size Zn used as a precursor in tracing (a) and the X-ray diffraction spectrum of nanoparticles of $ZnO_2$ in tracing (b) that were produced by PLA using micro size Zn as a precursor.

FIG. 2 shows the XRD spectrum of (a) the micro zinc precursor, and (b) the $ZnO_2$ nanoparticles synthesized in powder form using the pulsed laser ablation technique. The XRD spectrum of $ZnO_2$ nanoparticles, as presented in FIG. 2, clearly shows the crystalline structure of the nanoparticles, indicating various peaks of zinc peroxide ($ZnO_2$). The main dominant peaks for $ZnO_2$ were identified at 2θ=31.61°, 36.79°, 53.17° and 63.21° C., respectively, which correspond to indexes (111), (200), (220) and (311), respectively. The average grain size 'd' of the nanoparticle of $ZnO_2$ was estimated by using the Scherrer equation:

$$d = \frac{0.9\lambda}{\beta\cos\theta}$$

where λ=wavelength of the X-ray, β=FWHM (Full Width at Half Maximum) width of the diffraction peak, and θ=diffraction angle.

The lattice parameter of the $ZnO_2$ nanoparticles was estimated using the following formula of the cubic structure:

$$a = \frac{\lambda}{2\sin\theta}\sqrt{h^2 + k^2 + l^2}$$

The grain size estimated by using the Scherrer equation was 4 nm, and the lattice parameter was 4.8620 □ for the $ZnO_2$ nanoparticles prepared by pulsed laser ablation in 3% $H_2O_2$.

Figure 3:
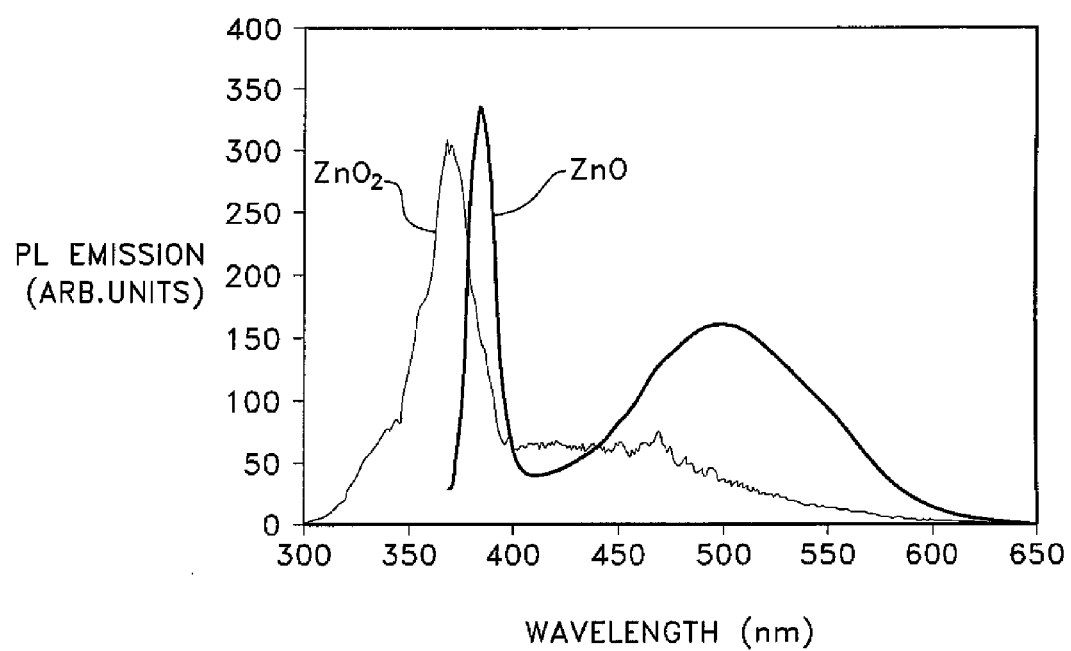
FIG. 3 shows a comparison of the photoluminescence spectra of ZnO nanoparticles and $ZnO_2$ nanoparticles produced by PLA using micro size Zn in pure de-ionized water and in 3% $H_2O_2$, respectively.

FIG. 3 shows typical PL spectra for the ZnO and $ZnO_2$ nanoparticles prepared by the PLA method described above using microstructured zinc in deionized water and in 3% $H_2O_2$, respectively. The PL spectrum of ZnO consists of two peaks, one located at 383 nm (3.25 eV) in the UV region, which is due to the near band edge emission of the wide band gap ZnO, and the other peak is a broad peak centered at 500 nm that occurs in the visible region. It has been reported that visible emission from nanostructure ZnO particles is due to oxygen defects, and it is clear that the stronger the visible emission, the lower the quality of the ZnO crystal is. On the other hand, $ZnO_2$ shows a strong emission peak centered at 369 nm, and a weak peak was also observed at 470 nm. The absence of green-yellow emission in our $ZnO_2$ nanoparticles indicates the unique feature of our synthetic method, which produces a low concentration of oxygen defects and high optical quality $ZnO_2$ nanomaterial. In addition, there is a blue shift in the UV emission peak, which is due to a quantum confinement effect.

Figure 4:
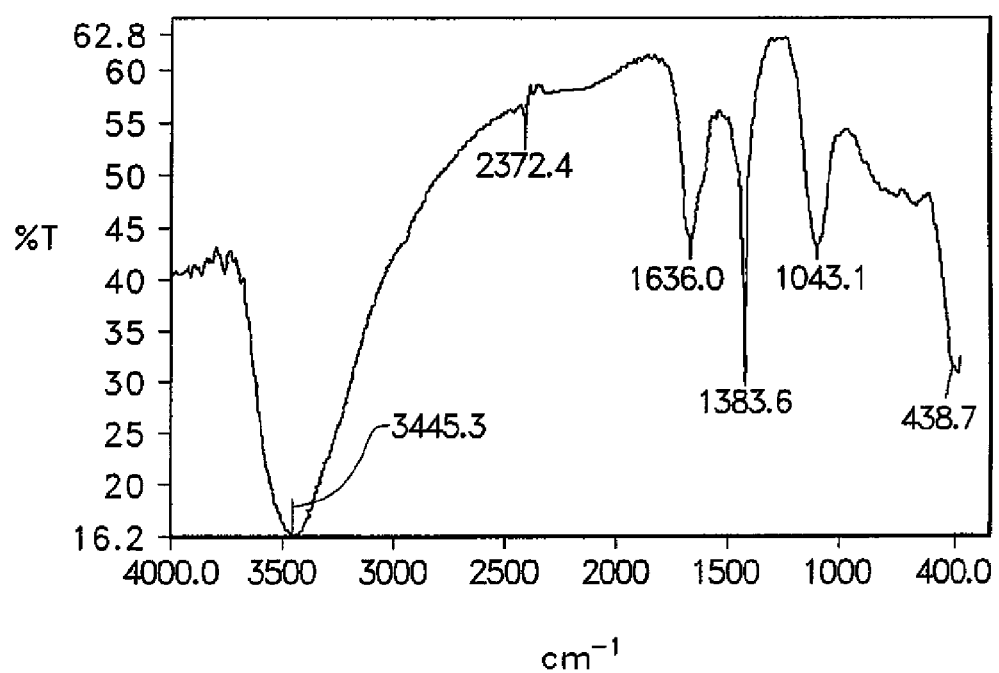
FIG. 4 shows the FTIR spectra of $ZnO_2$ nanoparticles prepared by laser ablation.

In order to confirm the purity of the nanoparticles of $ZnO_2$ synthesized by our method, the Fourier Transform Infrared (FTIR) spectrum was studied carefully in the spectral range of 400-4000 $cm^{-1}$. FIG. 4 shows the FTIR spectrum of $ZnO_2$ nanoparticles prepared in aqueous solution. The spectrum shows a characteristic $ZnO_2$ absorption at 438 $cm^{-1}$ for the nanoparticles. There is also another band at 1048 $cm^{-1}$, which most probably arises from the O—O bands. The absorption peak at 3200-3600 $cm^{-1}$ is attributed to the water O—H stretching vibration mode. The band at 1636 $cm^{-1}$ is due to the OH bending of water. This indicates the presence of a small amount of water adsorbed on the nanoparticle surface. Because of the presence of molecular $CO_2$ in air, there is an absorption peak at around 2372 $cm^{-1}$.

Figure 5:
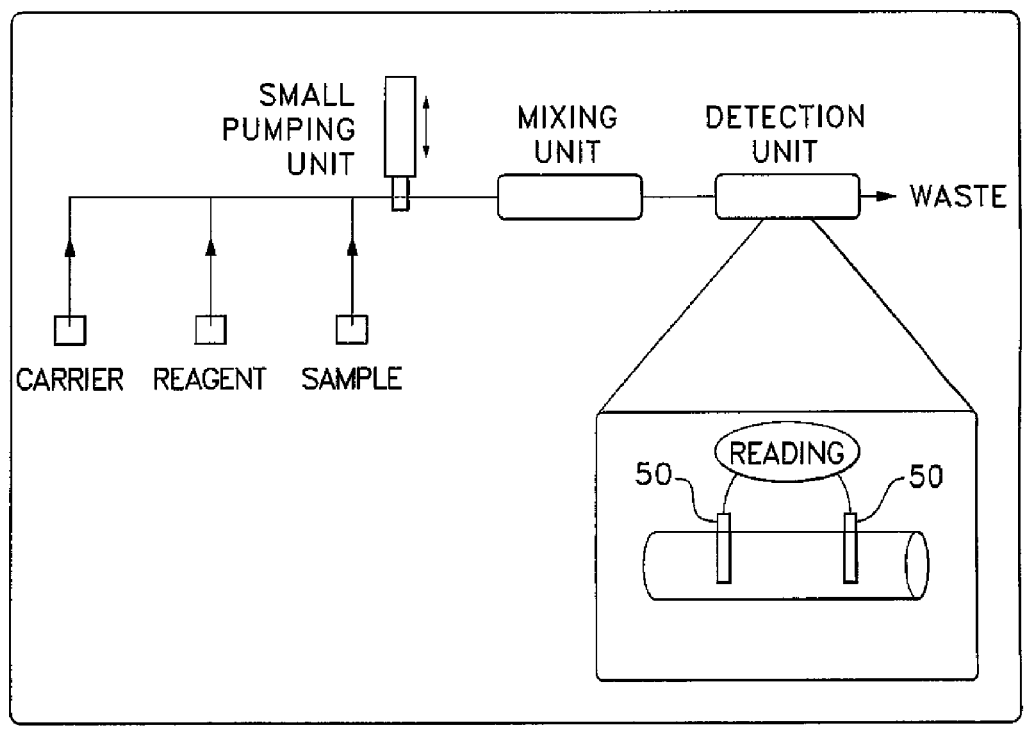
FIG. 5 is a schematic diagram of an experimental setup for the detection of cyanide in water using a $ZnO_2$ nanoparticle-coated electrode as a sensor according to the method of the present invention.

The setup for cyanide detection applied in this work comprised a small pump combined with a mixing unit and a detection unit, as shown in FIG. 5. The major components in this detection unit include $ZnO_2$-coated electrodes 50 and a potentiometer (although the term "potentiometer" is often used to refer to a variable resistor similar to a rheostat, here it refers to an instrument for measuring potential or voltage using a constant current d.c. supply and a galvanometer, in addition to a variable resistor).

All reagents and standard cyanide solutions were prepared from analytical grade chemicals of high purity (99.99%). Deionized water was used for preparation of the solutions.

The reagents were stored in polythene vessels. Because of the toxicity of cyanide, all solutions were carefully handled in the fume hood as a safety precaution. Also, direct contact with the cyanide, ingestion and/or inhalation of the cyanide solutions was avoided.

The following were the procedures for preparation of the test solutions. Cyanide solutions were freshly prepared by dilution from stock solutions by weighing 0.25 g of standard Fisher potassium cyanide and dissolving the salt in deionized distilled water in a standard flask to generate 1000 ppm of stock solution. A series of standard concentrations of cyanide for the experiments was prepared from this stock solution by further dilutions.

A $ZnO_2$ nanoparticle suspension was prepared by adding 10 mg of accurately weighed $ZnO_2$ nanoparticles to a 200 µL mixture of dimethyl formamide in the presence of Nafion, and then the mixture was ultrasonicated for 15 minutes to create a homogenous suspension. Prior to fabrication of the thin film, the electrode was cleaned by nitric acid, then kept in an ultrasonic bath for 5 minutes in acetone, then for 5 minutes in pure ethanol, and finally was rinsed 2-3 times with ultra-pure water and dried. After that, the electrode was immediately immersed in the $ZnO_2$ nanoparticle suspension for 1 hour. Then, the electrode was dried for 3 hours. Finally, the $ZnO_2$ nanoparticle-coated electrode was thoroughly rinsed with double-distilled water.

A schematic diagram the apparatus used to detect cyanide is depicted in FIG. 5. The following steps are the protocol applied for cyanide detection. A solution of potassium nitrate (the reagent) was linked to the pumping unit and aspirated. The test cyanide solutions were linked to the pumping unit and aspirated, then dispensed to the detection unit. A constant direct current was applied between two electrodes 50 coated with a thin film of the $ZnO_2$ nanoparticles, and the difference in potential was measured continuously using the potentiometer. The reaction is as follows:

$$ZnO_2 + CN^- \rightarrow OCN^- + ZnO \quad (1)$$

$$OCN^- + 2H_2O \rightarrow CO_2 + NH_3 + OH^- \quad (2)$$

For regeneration of zinc peroxide from zinc oxide $$ZnO + NO_3^- \rightarrow ZnO_2 + NO_2^- \quad (3)$$

Hence, the detector could regenerate itself and work indefinitely without any refurbishing.

Thus, by utilizing $ZnO_2$ nanoparticle-coated electrodes, a new kind of sensor has been developed for cyanide detection. In this sensor, the potential change is measured, which corresponds to the concentration of cyanide. Parametric Optimization was also carried out to find the optimum conditions that give large potential change, and eventually higher sensitivity for cyanide detection. The important physical parameters to control the reaction mechanism were also investigated. It was experimentally determined that the voltage response is directly proportional to the concentration of cyanide.

Figure 6:
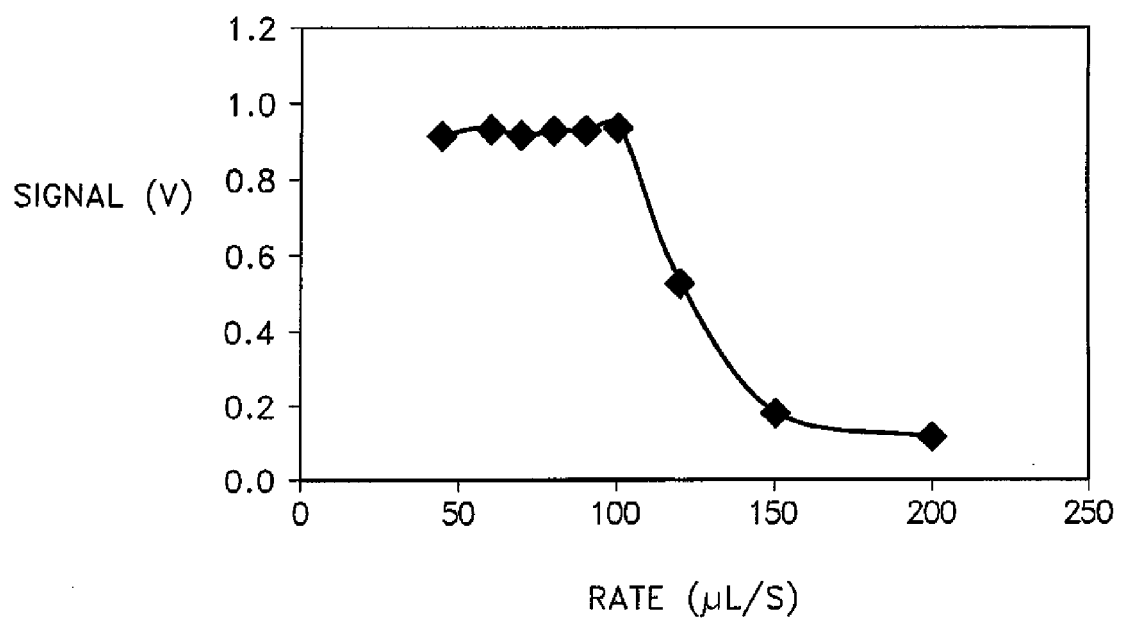
FIG. 6 is a chart showing the effect of the pumping rate of cyanide solution on the sensor signal of the electrode of FIG. 5.

The pumping rate of the solution to the detection unit should be adjusted in order to give appropriate time for the reaction between the $ZnO_2$ nanoparticle-coated electrode and cyanide to take place and to permit the change in potential. Therefore, the pumping rate was also optimized. A value of 100 µl s$^{-1}$ was found to be the optimum at which the electrodes gave a high signal, as depicted in FIG. 6. This indicates that $ZnO_2$ nanoparticles provide a fast response because of their structure stability and the small size of nanoparticles that provide a large surface area. Moreover, the small pores in the metal oxide could act as a substrate containing transport channels to decrease mass transfer resistance for an efficient catalytic process.

The reproducibility of the sensor performance was investigated by analyzing 10 samples, each having the same concentration of cyanide. The results of this analysis indicated that the $ZnO_2$ nanoparticle-coated electrode has a high reproducibility with a relative standard deviation (RSD) of 2.1%.

Figure 7:
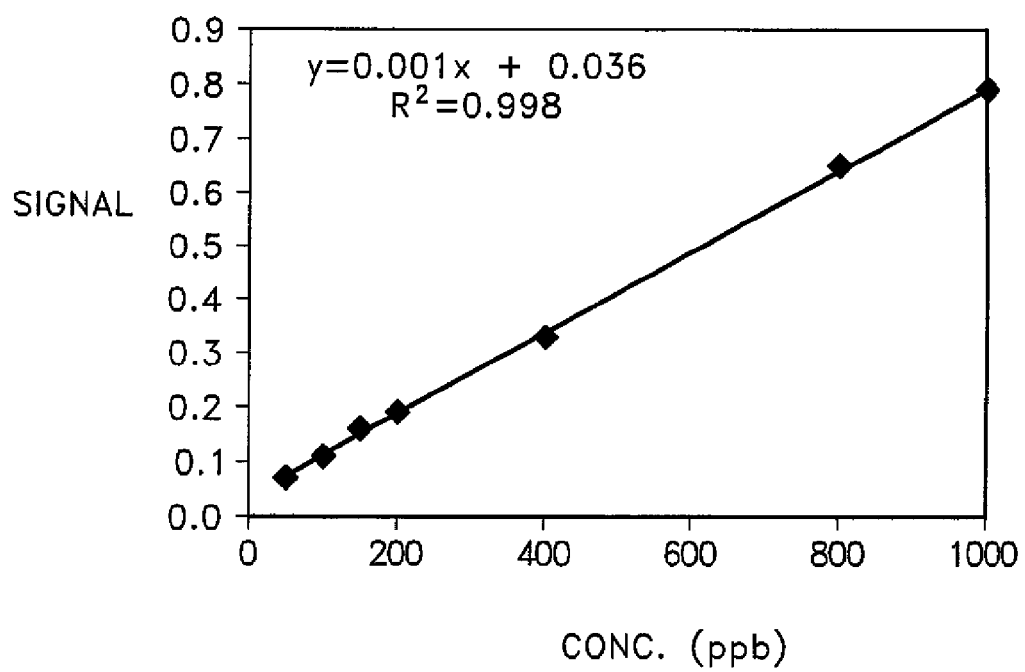
FIG. 7 is a chart showing the signal level produced by the electrode of FIG. 5 as a function of the concentration of cyanide in water, showing a linear correlation between concentration and signal strength.

The response of the sensor for different concentrations of cyanide was also investigated, and a chart showing the results is depicted in FIG. 7. As should be clear from FIG. 7, the response of the sensor was linear in the range between 50 ppb and 1 ppm with the correlation coefficient=0.998. The detection limit was found to be 50 ppb using the $ZnO_2$ nanoparticle-coated electrodes.

The chart of FIG. 7 may be considered a calibration curve for the electrode pair prepared in our laboratory, which could then be used to determine the cyanide concentration in a test sample of unknown concentration by interpolation of the linear response or calibration curve. The unknown test sample may be drinking water, wastewater, water from a stream adjacent an industrial plant using cyanide as part of an industrial process where there is a possibility of accidental discharge, etc.

It is to be understood that the present invention is not limited to the embodiments described above, but encompasses any and all embodiments within the scope of the following claims.

We claim:

1. A method for detection of cyanide in water, comprising the steps of:
preparing a calibration curve for a pair of electrodes coated with a thin film of $ZnO_2$ nanoparticles for serial dilutions of cyanide between about 50 parts per billion and 1 part per million;
aspirating components between a pump and a test cell with potassium nitrate;
pumping a sample of water into the test cell;
placing the pair of electrodes coated with the thin film of $ZnO_2$ nanoparticles in the test cell;
applying a constant current between the pair of electrodes coated with the thin film of $ZnO_2$ nanoparticles;
measuring the voltage between the pair of electrodes coated with the thin film of $ZnO_2$ nanoparticles; and
estimating the concentration of cyanide in the sample of water by interpolation of the measured voltage into the calibration curve.

* * * * *